United States Patent [19]

Roland et al.

[11] Patent Number: 4,665,306

[45] Date of Patent: May 12, 1987

[54] APPARATUS FOR ACTIVATING HEAT SHRINKABLE RIBBON ON DISPOSABLE GARMENTS AND OTHER ARTICLES

[75] Inventors: David R. Roland; Jerry A. Johnston; William S. Pomplun, all of Winnebago County, Wis.

[73] Assignee: Kimberly-Clark Corporation, Neenah, Wis.

[21] Appl. No.: 718,410

[22] Filed: Apr. 4, 1985

[51] Int. Cl.⁴ .......................... F27B 9/06; H05B 3/62
[52] U.S. Cl. ................................ 219/388; 425/174.4; 219/411; 219/343
[58] Field of Search ............... 219/388, 354, 405, 411, 219/343, 400, 403, 388 S, 402; 198/803.13, 484.1; 264/230, DIG. 71; 425/174.4; 156/85, 161, 164

[56] References Cited

U.S. PATENT DOCUMENTS

| 1,308,837 | 7/1919 | Blakeney | 198/803.13 |
| 2,100,441 | 11/1937 | Greene | 198/484.1 |
| 2,186,566 | 1/1940 | Albright | 198/803.13 |
| 2,639,025 | 5/1953 | Schmitt | 198/803.13 |
| 2,674,809 | 4/1954 | Meienhofer | 219/388 |
| 3,245,407 | 4/1966 | Mason | 128/284 |
| 3,639,917 | 2/1972 | Althouse | 2/270 |
| 3,818,181 | 6/1974 | Benard | 219/403 |
| 3,912,565 | 10/1975 | Koch et al. | 156/85 |
| 4,050,462 | 9/1977 | Woon et al. | 128/287 |
| 4,300,967 | 11/1981 | Sigl | 156/164 |
| 4,333,003 | 6/1982 | Rivera | 219/343 |
| 4,565,917 | 1/1986 | Furtek | 219/388 |

FOREIGN PATENT DOCUMENTS 2016262 2/1979 United Kingdom .

OTHER PUBLICATIONS

Perrotta, Frank, "Heating With Far Infra—red", Plastics Engineering, Modern Plastics, Aug. 1953, pp. 109–111, 114, 115.

Primary Examiner—E. A. Goldberg
Assistant Examiner—Teresa J. Walberg
Attorney, Agent, or Firm—Paul Yee

[57] ABSTRACT

Apparatus for activating heat shrinkable ribbon on disposable garments and other articles in which the ribbon is absorbent of electromagnetic radiation and is bombarded by infrared rays for a time long enough to activate and shrink the ribbon. Heated convection air may be directed past the infrared radiators toward the ribbon to cool the radiators and maintain a desired spectral distribution of the radiation.

12 Claims, 15 Drawing Figures

APPARATUS FOR ACTIVATING HEAT SHRINKABLE RIBBON ON DISPOSABLE GARMENTS AND OTHER ARTICLES

TECHNICAL FIELD

This invention relates generally to methods and apparatus for the formation of gathered elasticized portions of articles, for example, an elasticized body-encircling portion of a disposable garment.

BACKGROUND

Numerous articles which are designed for single use or temporary use have become commercially important in recent years. These articles are meant to be disposed of after being used once instead of being laundered or cleaned for re-use. Examples of garments of this general type are disposable diapers; adult incontinence garments; disposable bed sheets; disposable shower caps; garments intended for single use in hospitals such as surgical gowns, surgical hats and booties; and single use or disposable pajamas and the like intended to be worn by patients in a hospital for a short stay. Articles other than garments are also within this class, such as protective covers, dust covers, etc. Single use or disposable articles of this type are made of lightweight film or sheet materials such as thermoplastic films, nonwoven fabrics of various materials such as thermoplastic or cellulosic fibers, paper, coated film or paper, and various composites of one or more of these types of materials such as disposable diapers which include, for example, layers of polyethylene and polypropylene which sandwich an absorbent material or fluff. These garment materials are distinguishable from textiles used to make a sewn garment or article which is intended for long term use and subject to repeated laundering or dry cleaning.

Disposable articles of the type under consideration are economically feasible only when they can be manufactured at high production rates using techniques typical of converting film materials, such as heat sealing, sonic sealing, adhesive bonding, etc., instead of the sewing techniques customary with textile garments meant for long term use. Even with the disposable articles, however, it is often desirable to form an elasticized portion in order to provide a snug fit. In the case of disposable garments intended to be worn by human beings, for example, it may be necessary to provide a gown or similar item with elasticized wrists, or to produce a disposable diaper with elasticized waist portions and leg portions in order to provide a snug fit, or to provide disposable booties with an elasticized ankle encircling portion. In the case of other products such as bed sheets and dust covers, a marginal portion that can fit snugly about an article with which the product is used is often required.

Because articles of this type need to be made at high production speeds, the formation of an elasticized portion by sewing in a strip of elastic material as is common in the production of textile garments is not practical. Furthermore, in the case of disposable diapers, for example, which have an "hour glass" or generally "I-shaped" configuration, difficulty is encountered when attempting to apply elastomeric material to both the legbands and waistbands. Application to the legbands has been commercially achieved. However, application to the waistbands on the same diaper causes problems.

Among the methods that have been developed or proposed in the art to form elasticized portions of disposable products are several which involve the use of heat, such as (1) constructing the article of an oriented thermoplastic film and contact heating selected portions thereof to cause them to heatshrink and form integral elastic portions (see U.S. Pat. No. 3,245,407); (2) applying a tape to the article that is elastic at room temperature but rendered inelastic at elevated temperatures and heating selected portions of the tape to kill its elasticity (see U.S. Pat. No. 4,300,967 and published United Kingdom patent application No. 2,016,262); and (3) applying a tape of a material that is inelastic at room temperature but rendered elastic by the application of heat (see U.S. Pat. Nos. 3,639,917 and 3,912,565).

The method disclosure of U.S. Pat. No. 3,639,917 involves heating a garment section bearing heat recoverable elastomeric tape to temperatures in the range of 75° C. to 150° C. (167° F. to 302° F.) such as by use of a hot air gun, iron or an oven. U.S. Pat. No. 3,912,565 discloses forming an elasticized article by heating heat shrinkable uniaxially oriented polyurethane tape to a temperature slightly above its second order phase transition temperature, 100° C. (212° F.) being disclosed as an operable temperature; for this purposes, the patent states the heat may be applied by gas, such as hot air, or liquid.

In U.S. Pat. No. 3,912,565, the tape is disclosed as stretched by application of external heat, cooled at the stretched condition, then again heated by application of external heat to effect controlled heat shrinkage. In U.S. Pat. No. 3,639,917, block copolymers are irradiated, then expanded at elevated temperatures to achieve a new length, then cooled to maintain the copolymers at the new length. Subsequent reheating returns the copolymers to their original length.

DISCLOSURE OF THE INVENTION

A new process for forming an elasticized marginal portion of an article is provided in which a strip, ribbon, tape or the like of thermally-elasticizable material is attached to the article along or near a marginal portion that is to be elasticized. The material has potential elastic energy which is created, for example when the material is oriented, either by machine direction stretching or compression rolling, and which can be recovered by heating the oriented strip to its activation temperature. When so heated, the oriented strip shrinks causing an increase in elastic elongation and retractive properties necessary for elasticization of the marginal portion of the article.

The articles are formed on a high speed production assembly with the oriented strips in place. During the heat shrink phase, the strips are in an unrestrained state so as not to inhibit shrinking and are presented outwardly of the articles. The strips are heated to recover their elastic energy by controlled infrared radiation which acts on the strips with minimal effect on the rest of the article or on the environment. This step is performed in a manner which provides substantially no interruption to production of the article. In addition, heated air may be utilized to assist in heating the strips.

Also developed is an apparatus for practice of the method which includes infrared radiation means for generating and directing infrared rays, means for substantially-continuously carrying articles having oriented strips in place thereon past the infrared radiation means, the conveying means being constructed to present the strips outwardly of the articles and in an unrestrained state, and the infrared radiation means being positioned facing the strips for irradiating the strips by infrared rays, whereby the strips are heated to recover their elastic energy. Means for causing heated air to be directed at the oriented strips may also be provided to assist in heating the strips.

The method and apparatus for this invention provide new and useful results, as explained in the description which follows, which in part will be obvious from the description, or which may be learned by practice of the invention. The objects and advantages of the invention may be realized and attained by means of the instrumentalities and combinations particularly pointed out in the appended claims.

BEST MODES FOR CARRYING OUT THE INVENTION

The drawings depict the method and apparatus for this invention employed in the formation of elasticized waist portions of a disposable infant's diaper, which is a particularly useful application of the present invention. However, it should be borne in mind that this invention can be practiced advantageously with numerous other types of articles and that the diaper is described herein in an exemplary, not limiting, sense.

The detailed description is divided into four parts: (a) a background discussion, (b) a method description, (c) an apparatus description, and (d) a description of operational conditions.

(a) Background

Figure 1:
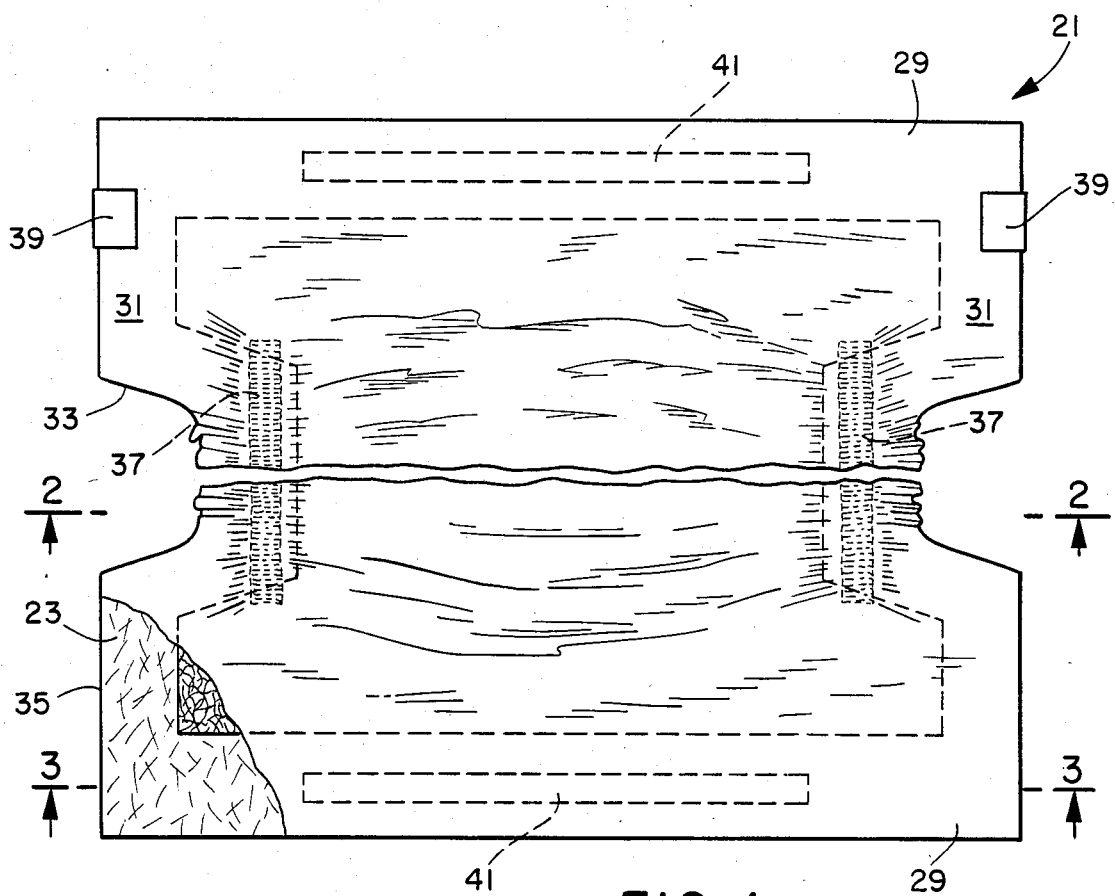
FIG. 1 is a plan view, with portions broken away, of an infant's disposable diaper as an example of a type of article with which the present invention may be practiced.
Figure 2:
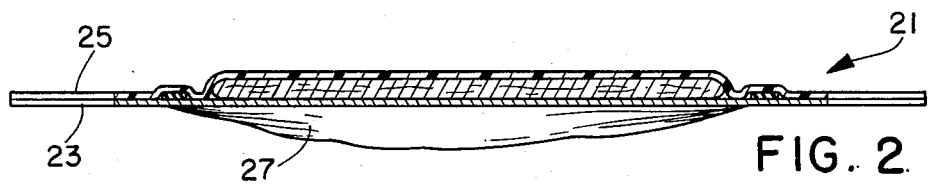
FIG. 2 is a sectional view of the diaper of FIG. 1 taken along the plane of line 2—2.
Figure 3:
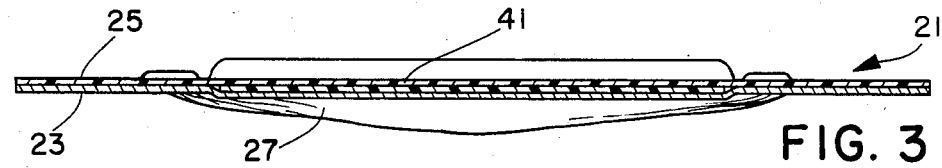
FIG. 3 is a sectional view of the diaper of FIG. 1 taken along the plane of line 3—3.

FIGS. 1, 2 and 3 illustrate a disposable diaper 21 comprising a liquid-permeable inner liner 23, a liquid-impermeable outer layer 25, and an absorbent batt 27 secured therebetween. The inner liner 23 and outer layer 25 are larger than the absorbent batt 27 and have end marginal portions 29 extending beyond the ends of the batt and side marginal portions 31 extending beyond the sides of the batt. The liner 23 and outer layer 25 are secured to each other along the marginal portions 29 and 31. Conventional materials are used for these elements of the diaper 21. The inner liner 23 may be any soft, flexible porous sheet which passes fluids therethrough and may comprise a nonwoven web or sheet of polyolefin fibers such as polypropylene, wet strength tissue paper, a spun woven filament sheet, etc. It may be treated with a surfactant to aid in liquid transfer. The outer layer 25 is a liquid-impermeable layer and may comprise a thin web or sheet of plastic film such as polyethylene, polypropylene, polyvinyl chloride or the like; it may be transparent or have an embossed or matte surface to be opaque. The absorbent batt 27 may be of any suitable material, generally cellulosic material, such as an airformed batt of wood pulp fibers commonly known as "fluff", being preferred.

The inner liner 23, outer layer 25 and batt 27 may be combined with one another in any suitable manner to form the finished diaper. The elements may be bonded to one another by means of strips or patterns of hot melt or pressure sensitive adhesive, overall or patterned heat sealing, strips of double faced pressure sensitive adhesive tape, etc. A particularly effective bonding system is the use of spaced parallel lines of hot melt adhesive on the interior surface of the outer layer 25, with the absorbent batt bonded to the layer 25 along sections of the lines of adhesive and the inner liner 23 bonded to the layer 25 along other sections of the lines of adhesive within the marginal portions 29 and 31 outside the batt.

The diaper is of a generally hourglass or I shape including a central narrowed crotch section 33 and waistband sections 35 along each end thereof. Elongate elastic means 37 are secured in place adjacent the absorbent batt 27 on each side thereof to develop gathered elastic leg portions that are conformable with an infant's legs. Conventional pressure sensitive tapes 39 are attached to one waistband section 35. The diaper 21 is fitted to an infant with the inner layer 23 against the child's skin; one marginal portion 29 encircles part of the infant's waist and the other marginal portion 29 encircles the balance, with the two being overlapped and joined together by the pressure sensitive adhesive tapes 39 in order to hold the diaper in place.

The structure of diaper 21 as described to this point forms no part of the present invention, and further details of its construction may be had by reference, for example, to U.S. Pat. No. 4,050,462.

(b) Method Description

For the purposes of the present invention, the diaper 21 of FIGS. 1-3 includes thermally-elasticizable strips of ribbons 41 which are secured to the interior surface of the outer layer 25, best seen in FIG. 3, there being one ribbon 41 positioned within each end marginal portion 29 spaced inwardly from the outer edge thereof. The ribbons 41 have a selected width and selected length, about ¼" to 1" wide being suitable for most articles and the length being as long as required for the particular article to which the ribbons are applied. A ribbon 41 usually will be relatively thin, approximately 0.75 to 10 mils being suitable in most instances, although these dimensions are not critical.

Figure 4:
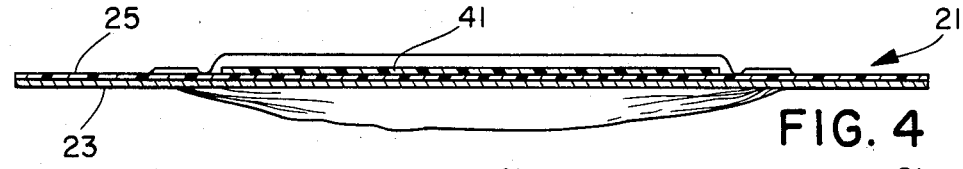
FIG. 4 is a sectional view the same as FIG. 3 illustrating a second structure of the diaper of FIG. 1 suitable for the practice of this invention.
Figure 5:
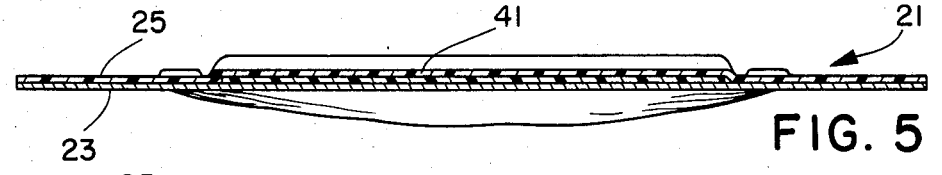
FIG. 5 is a sectional view the same as FIG. 3 illustrating a third structure of the diaper of FIG. 1 suitable for practice of this invention.
Figure 6:
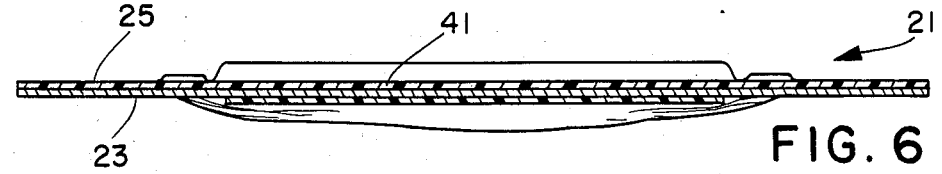
FIG. 6 is a sectional view the same as FIG. 3 illustrating a fourth structure of the diaper of FIG. 1 suitable for the practice of this invention.

FIGS. 4-6 show alternate positions for the ribbons 41 which also are suitable: the exterior surface of the outer layer 25 (FIG. 4), the interior surface of the liner 23 (FIG. 5), and the exterior surface of the liner 23 (FIG. 6).

A thermally-elasticizable ribbon 41 may be secured to the liner 23 or other layer 25 by any suitable means, but most usefully by pressure sensitive adhesive on the surface of the ribbon 41 which is to contact the inner liner or outer layer. The pressure sensitive adhesive may be physically disposed on such surface in the form of one or more spaced parallel lines of adhesive extending longitudinally of the ribbon 41, or as a ribbon, layer or pattern of adhesive on such surface of the element. The adhesive may be any pressure sensitive adhesive appropriate to the type of materials employed for the ribbon 41 and the layer to which it is to be secured, such as a hot melt pressure sensitive adhesive.

The thermally-elasticizable ribbon 41 is to be made of a material that is relatively inelastic at room or ambient temperature but which is capable of being rendered elastic when heated to an elevated temperature, and remaining elastic when cooled back to room temperature. Thus, the ribbon 41 is to be made of a thermally-activated elastic material, i.e., a material that becomes elastic upon thermal activation. As used in this description and the claims, the term "elastic" is defined to mean that ribbon 41 can be manually elongated from about 125% to about 200% of its original length and will return to substantially its original length upon release of the force causing the elongation.

One type of material particularly suitable for the thermally-elasticizable ribbon 41 is, in the present invention, a co-extruded film having an inner layer of a polyether block amide resin composed of linear regular chains of rigid polyamide segments and flexible polyether segments, such as is produced from the commercially-available Pebax (Trademark) resins sold by ATO CHEM, and outer layers of ethylene/vinyl acetate (EVA) copolymer and its ionomeric adducts, and ethylene/acrylic acid (EAA) copolymers. This type of material can be oriented, i.e., stretched or rolled in one direction without the application of external heat to a length so that when the applied tension is removed, the elastomer relaxes to a permanent deformation length greater than its original length yet less than the stretched length. This deformation length is sometimes referred to as a preform. Upon subsequent application of heat, the elastomer shrinks and recovers or assumes its elastic properties. Thermally-elasticizable material of this type is more fully described in the co-pending U.S. patent application, Ser. No. 606,082, entitled Heat-Shrinkable Elastomer, Method of Producing the Elastomer and Articles Utilizing the Elastomer, assigned to the assignee of this application, the disclosure of which is incorporated herein by reference. This thermally-elasticizable material is rendered elastic when hated to a temperature range of about 125° F. to 230° F., preferably in the range of about 180° F. to 200° F., and retains its elasticity when cooled back to room temperature subsequent to heating.

Other materials which may be suitable for the ribbon 41 includes polyurethanes which are based upon polyethers and polyesters, ethylene/vinyl acetate copolymers, modified natural rubber elastomers, polyester block amides, polyvinyl chlorides, polyester polyether copolymers, ethylene/propylene copolymers and blends. Also useful are complex composite materials constructed of EVA polyethylene/polyvinyl acetate copolymers with heat sealed polyurethane (pretensioned) threads, such as KER 2207 marketed by 3M Company. In the case of natural rubber elastomers, heat is applied during initial stretching with vulcanization so that the material is chemically cross-linked to hold it in place in the stretched condition. Subsequent reheating breaks the cross-linking and causes the material to shrink. As will be described below, the foregoing materials and the preferred material described above are particularly advantageous for the reason that they contain a chemical structure which is excited by the infrared radiation causing the ribbons 41 to be heated to the activation temperature, while the associated other materials (layers 23, 25, 27) and the surrounding environment remain substantially unaffected.

Figure 7A:
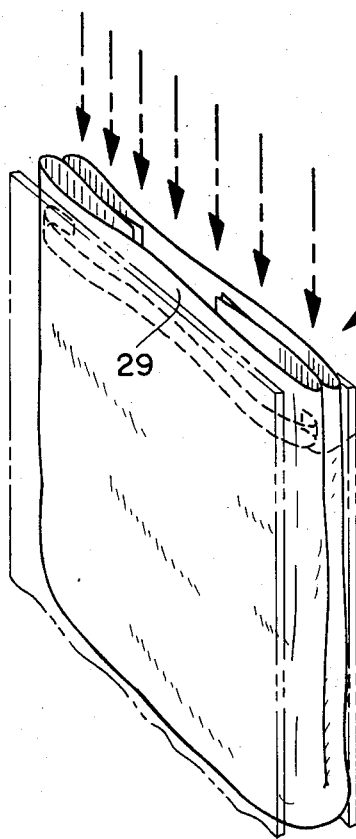
FIGS. 7A, 7B and 7C are perspective views illustrating sequential stages in the processing of one of a stack of diapers of FIG. 1 according to the method of this invention.
Figure 7B:
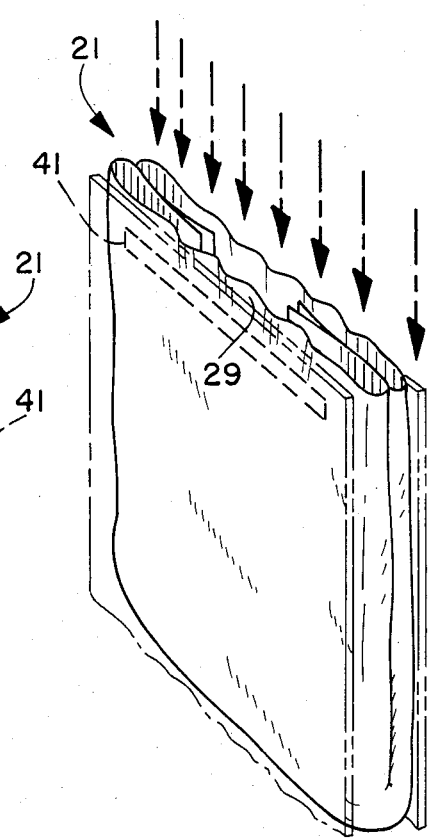
Figure 7C:
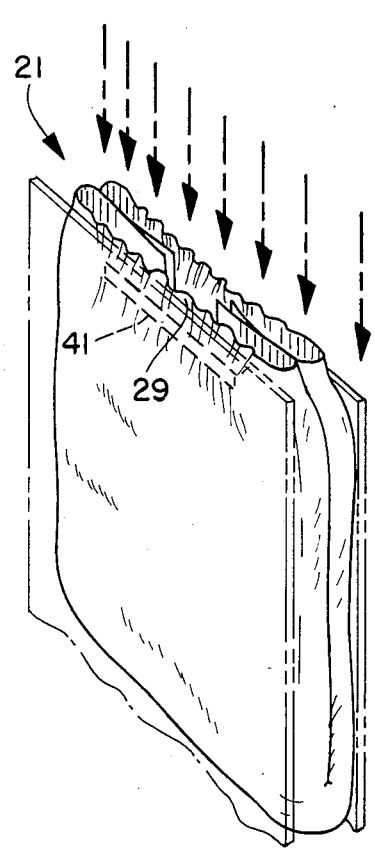

FIGS. 7A, 7B and 7C illustrate the processing of diapers 21 in accordance with the method of this invention. While the arrows indicate the general direction of the incident radiation, it is readily apparent that the radiation can also impinge the article at a plurality of angles and directions other than the single direction shown.

Diapers 21, after formation and with the stretched unelasticized ribbons 41 positioned within each end marginal portion 29, are folded longitudinally and then folded in half transversely to a rather narrow width. It is useful to fold the diapers sufficiently narrow, as shown in FIG. 7A, to bend the ribbons 41 around the folded side portions of the diapers. The diapers are thusly folded and stacked (horizontally or vertically) in a manner so that their end marginal portions 29, along which the ribbons 41 are secured, are positioned adjacent one another and face outwardly. It is useful to form a stack of a number of folded diapers having their marginal portions 29 substantially parallel to one another in order to increase production rates, but the articles may also be processed one at a time if so desired.

For the practice of this invention, infrared radiation irradiates the marginal portions 29 and heats the thermally-elasticizable ribbons 41 to their activation temperature, i.e., a temperature above which elasticity is restored to the ribbon material. Heated convection air may also be directed at the ribbons 41 to assist in heating them. The infrared radiation and the assisting convection air heats the outer poly layer softening it to minimize resistance to contraction of the ribbon. The radiation has a minimal effect on the other parts of the diapers to which the ribbons 41 are secured which might damage the material layers, and has a minimal effect on the environment or other structure in the vicinity.

In accordance with the invention, the infrared radiation includes emitted radiation at wavelengths and at a power level operable to excite and generate heat within the ribbon 41. In the preferred form described herein, the coextruded polyether block amide (PEBA) and EVA ionomer (skin) material contains carbonyl, ether, amide and methylene functional groups in the skin and core layers, which have been found to be highly absorptive of electromagnetic radiation at wavelengths of from about 1.0 to about 14.0, preferably about 5.7 to about 5.9 microns. Irradiation of the PEBA material by electromagnetic radiation containing a sufficient level of emitted power at this wavelength range operates to heat the material to its activation temperature.

Emitted radiation from radiation sources such as from quartz tungsten filament lamps and ceramic heaters, which have been found particularly useful, contains a wide distribution of radiation wavelengths. The wavelengths of such emitted radiation vary according to the operating temperature of the emitter and is illustrated by plotted curves from selected source temperatures appearing in FIG. 10.

Figure 10:
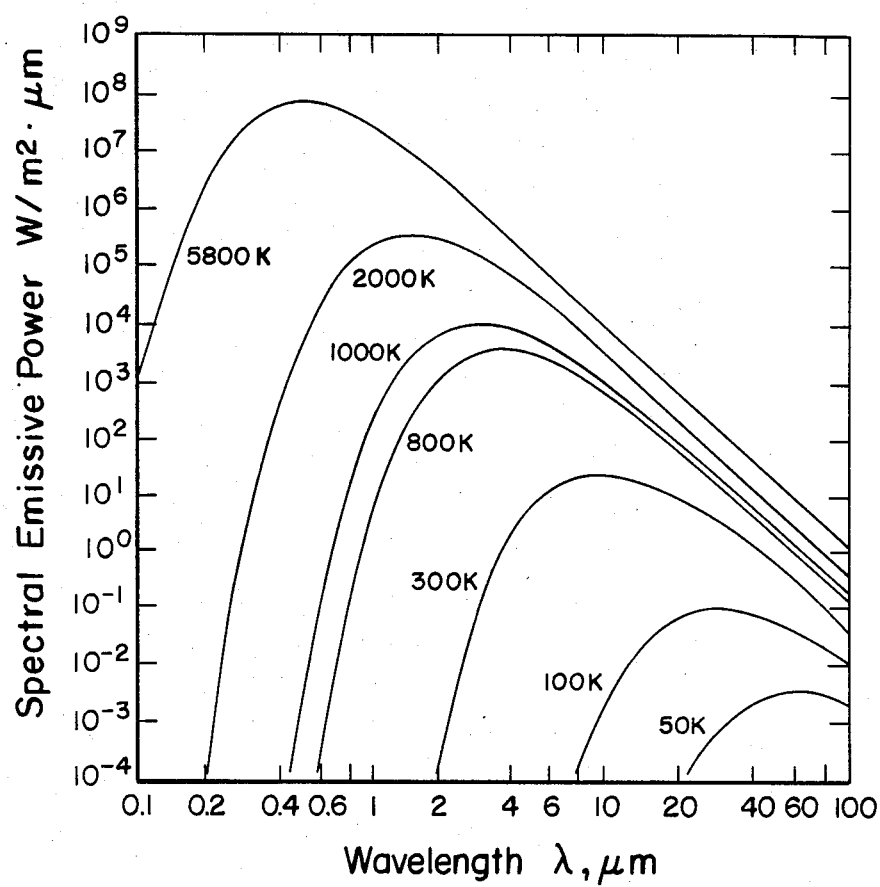
FIG. 10 representatively shows plots of spectral emissive power as a function of the wavelength of the emitted radiation for various emitter temperatures.

The curves of FIG. 10 were plotted for selected temperatures based upon the Planck distribution which is the spectral distribution of radiation intensity associated with blackbody emission.

From the curves in FIG. 10, it is seen that peak wavelengths in the preferred range, i.e., 5.7 to 5.9 microns, can be achieved with an emitter temperature of between 300° K. and 800° K. However, there is a higher power output of the radiation source at the preferred wavelength range when using a radiation source which operates at a higher temperature and which has a peak wavelength range less than 5.7 microns.

Figure 11:
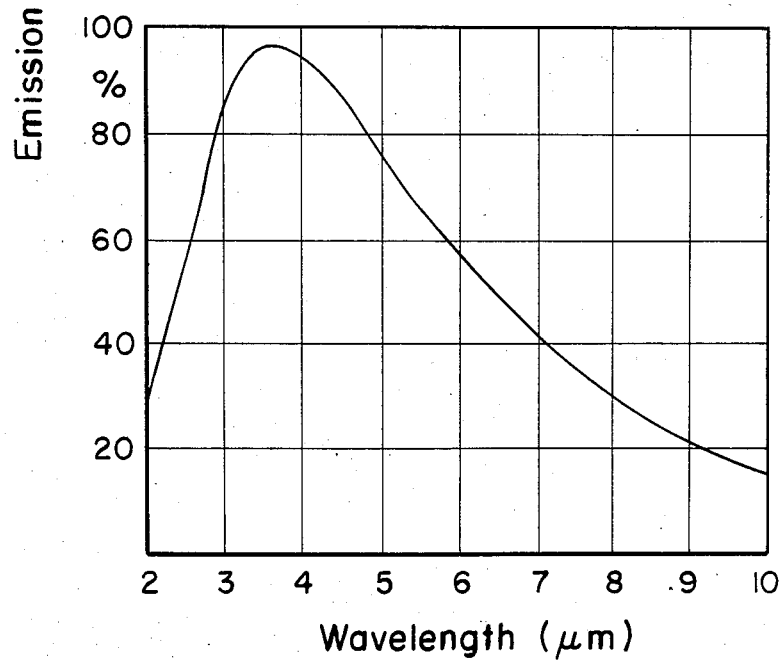
FIG. 11 shows a representative emission spectrum of a ceramic type radiation source.

A commercially available ceramic heater radiation type source operating at 510° C. can produce an emission spectrum as shown in FIG. 11. A suitable device is produced by GTE Sylvania, Exeter, N.H.

Peak wavelengths and main wavelengths of such ceramic heaters can be determined from available technical literature. For example, the ordinates of FIG. 12 depict power ratings for two different commercial ceramic radiators; models FSR/245 and FSR/122 manufactured by GTE Sylvania.

Figure 12:
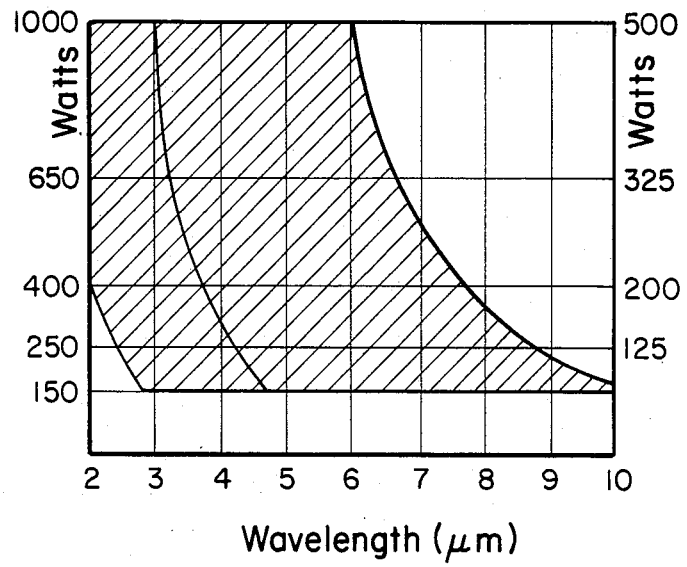
FIG. 12 shows plots of peak wavelengths and main wavelengths for two different commercial ceramic radiators.

The shaded area of FIG. 12 shows the main wavelengths and the curve shows the peak wavelengths for those ceramic heaters. It can be seen from the graph in FIG. 12 that even though the peak wavelength of these heaters falls below the preferred range of this invention, these ceramic heaters can be very effective in emitting main wavelengths in the 5.7 to 5.9 micron range.

Figure 13:
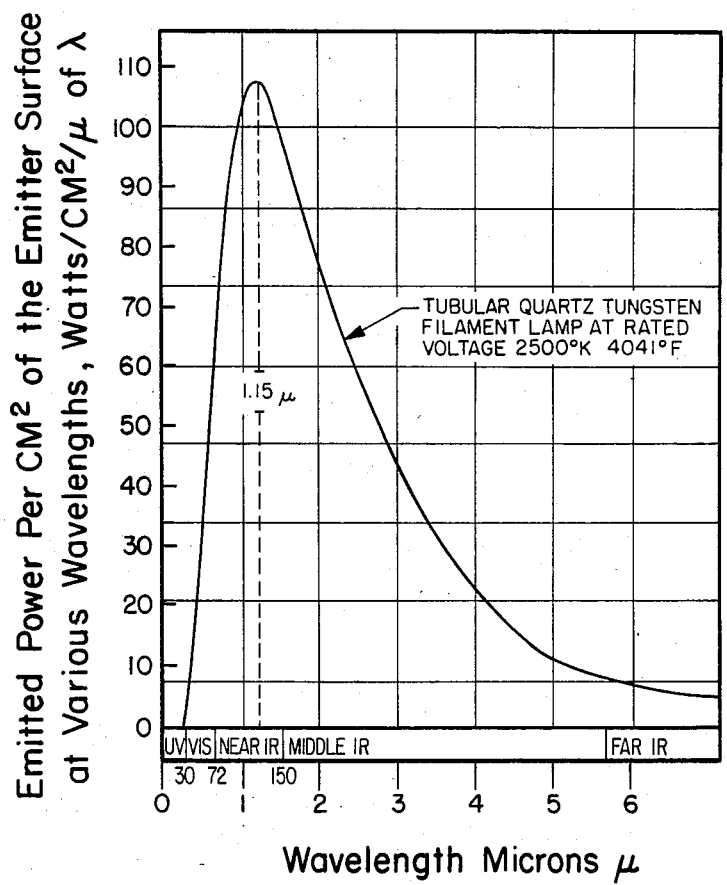
FIG. 13 shows a representative emission spectrum of a quartz-type radiator.

In the practice of this invention, in addition to ceramic heaters, quartz type radiant heaters having a spectral distribution according to the plotted curve in FIG. 13 have been used to heat elastomer waistbands constructed of extruded polyether block amide resin described above to their activation temperature.

For example, quartz-type, black body radiant emitters operating at about 1600 watts, which have a spectral distribution substantially as depicted in FIG. 13, can be employed in the practice of the present invention. Recirculating forced air blowers can be employed to cool the emitters to maintain a desired spectral distribution. At the same time the resultant heated air moving from the emitters is directed toward ribbons 41. Thus, the blown air is first directed past the radiant heaters and then directed toward the ribbons. The air cools the quartz heater elements and then heats the diaper marginal portion to soften it and facilitate shrinkage of the elastic. A warming of the outer liquid impermeable layer by absorption and convection assists in the shrinkage of the elastic.

Quartz radiant heaters of the type referred to are commercially available. Many of these utilize edge reflectors which aid in concentrating the radiant energy to a restricted area. Some also utilize forced air blowers, which as described above, can provide convection heating in addition to radiant heating and also provide for cooling of some of the parts. If desired, a separate source of heated convection air can be provided. In either case, this further enhances the efficiency of the process.

Ceramic heaters emitting main wavelengths and peak wavelengths as shown in FIGS. 11 and 12 also were used to heat ribbons of coextruded EVA ionomer/PEBA material on folded diapers to their activation temperature in the practice of this invention. In both cases, i.e., quartz and ceramic heaters, the heaters were spaced about 3–5 inches from the ribbons and required about 3 to 5 seconds exposure or "dwell time" to effect heat shrinking of the ribbons 41.

Importantly, it has been found that the elastomer functional groups in the compound material act as an absorber for the electromagnetic radiation so that the ribbon 41 primarily is heated by the infrared radiation. The outer poly layer is warmed which assists in the shrinking process. All in all, a highly efficient process results.

It is desirable that the spacing between the heaters and the articles be adjustable. Preferably, this is achieved by providing for adjustment of the heaters relative to the article conveyor by a convenient means which will be understood by those skilled in the art. For example, it may be necessary to shut down the diaper feeding means in which case the spacing should be adjusted to prevent possible adverse effect by the heaters on the diapers. Also, different sized articles, different materials, etc., may require that the spacing be adjusted as will be understood by those skilled in the art.

Processing of the diapers in the foregoing manner can be accomplished by transporting the diapers past a bank of radiant heaters so that the ribbons 41 are irradiated and heated by the emitted radiation rays and by convection air, if desired. The diapers preferably are arranged in a stack so that they are spaced from one another with marginal portions 29 and elastomer ribbons 41 unrestrained and facing outwardly and with the marginal portions 29 substantially parallel to one another and transverse to the travel direction. As illustrated in FIG. 7A, the radiant energy is beginning to heat the thermally-elasticizable ribbons 41 which, at this point, are substantially unaffected.

As the diapers 21 continue moving past the radiant energy source, as shown in FIG. 7B, the strips start to be rendered elastic, and thereby begin to contract, under the action of becoming heated by the absorption of radiant energy. Being unrestrained, the ribbons 41 are free to shrink as they become heated. Finally, see FIG. 7C, the ribbons 41 are rendered fully elastic and have contracted sufficiently that the free edge portions of the diapers have been gathered as shown. Heated convection air may be used to assist the action of the radiant energy source, both in heating the ribbons and in softening the outer poly layer, and may also be used to assist in cooling some parts, such as the heating elements of the radiant heaters.

Figure 8:
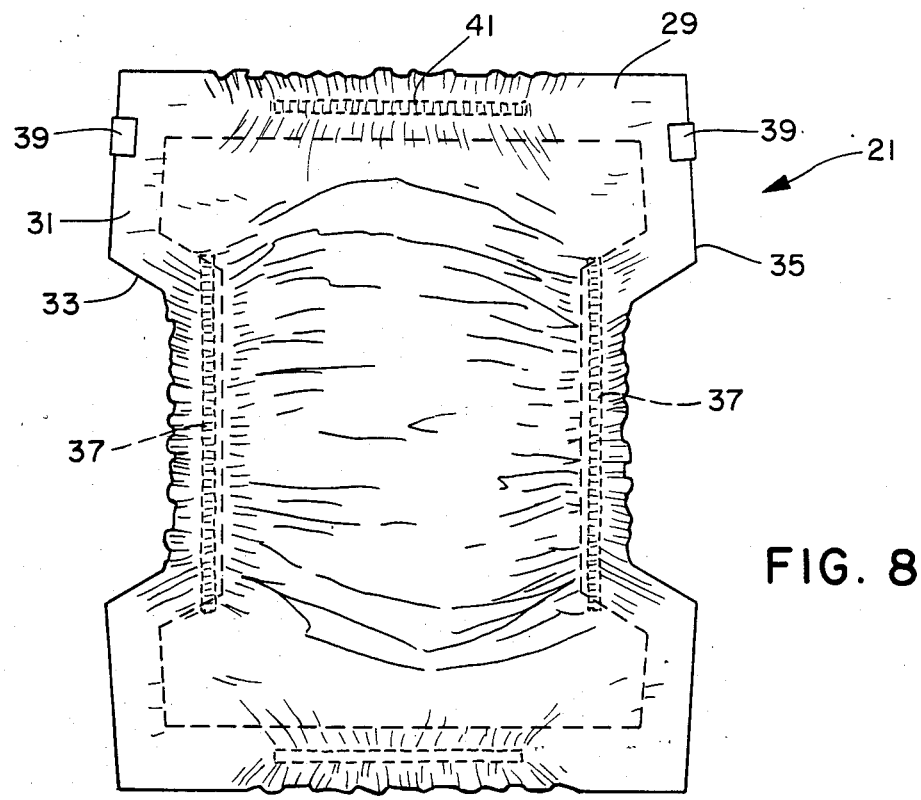
FIG. 8 is a plan view of the diaper of FIG. 1 after processing with the method of this invention.

Even though the elastomer strips become heated to their activation temperature, i.e., from about 120° F. to about 230° F., the remainder of the diapers remain relatively cool, as does the surrounding air, so that the generated energy is used most efficiently and is not wasted. After the stage of FIG. 7C, the diaper strips are allowed to cool back to ambient or room temperature. A finished diaper after being processed through the stages of FIGS. 7A–C and cooled is illustrated in FIG. 8. The ribbons 41 retain their elastic characteristic so that when a diaper is wrapped about an infant, the waist-encircling marginal portions 29 will provide a snug fit.

It will be appreciated that maximum efficiency and production rates can be maintained only if the heat-shrinking process described herein is carried out with no interruption or slow-down in the overall article formation process. Also, the required "dwell" time or time of exposure of the ribbons to infrared radiation and heated air is a function of the travel speed of the ribbons. By acting upon the ribbons with radiation and heated air at a stage of the process when the diapers have their marginal portions and ribbons substantially parallel to one another and transverse to the travel direction, maximum efficiency and production rates are achieved with a minimum of radiation heaters.

(c) Apparatus Description

Figure 9:
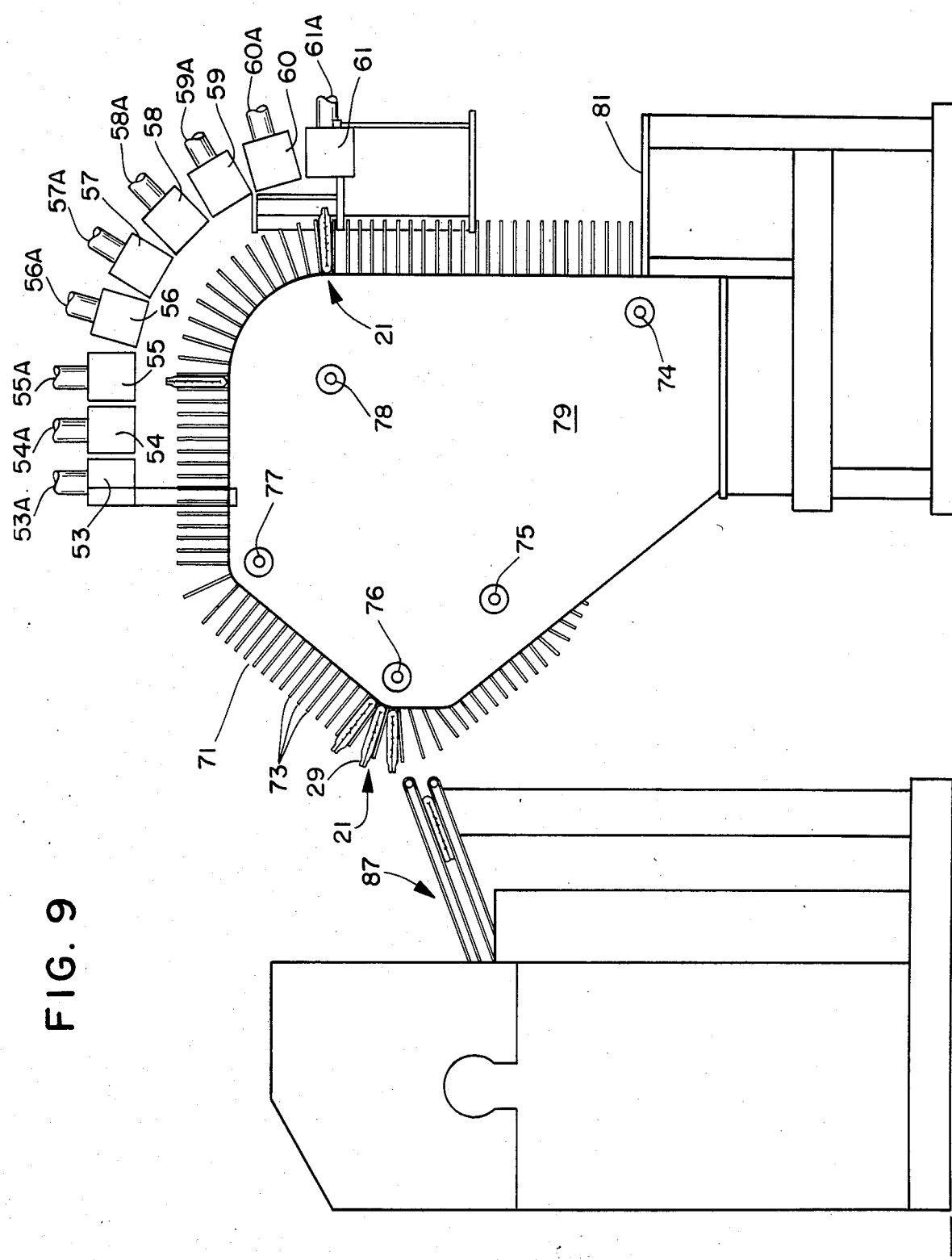
FIG. 9 is a side view of an apparatus of the present invention.

FIG. 9 illustrates an apparatus of this invention which is particularly useful for practicing the method described in part (b).

Referring to FIG. 9, the apparatus comprises infrared radiation means for generating and directing infrared rays indicated by the general reference numberal 51. As shown, the infrared radiation means includes a plurality or bank of modular infrared radiant heaters 53-61 arranged substantially side by side as shown. Although a "bank" of heaters is preferred, it will be understood that a single unit could be employed. The heaters 53-61 are constructed to generate and direct infrared rays of the desired wavelength and luminescence power toward the articles being processed (diapers 21) in a manner to be described.

In addition, heated convection air may be delivered past the heaters 53-61 to help cool the heating elements therein, and at the same time, to assist in heating the diapers 21, particularly in the case of quartz-type heaters. As shown in FIG. 9, the heated convection air can be delivered to and past the heaters 53-61 through conduits (ducts) 53A-61A, respectively.

In accordance with the invention, means is provided for substantially continuously carrying articles having shrinkable ribbons in place thereon past the infrared radiation means. The conveying means is constructed to hold the articles so that the ribbons are unrestrained and to present the ribbons outwardly of the articles, and the infrared radiation means is positioned facing the ribbons for heating the ribbons by infrared rays and heated air. In addition, the conveying means is constructed to hold the articles so that the shrinkable ribbons and the articles are disposed substantially parallel to one another and substantially transverse to the travel direction of the conveyor means.

As embodied herein, a stacker generally indicated by the reference numeral 71 is provided adjacent the bank of radiant heaters 53-61 for the purpose of arranging the diapers 21 in stacks for subsequent packaging. The stacker 71 includes a plurality of adjacent outwardly-extending, spaced paddles 73, which are carried by an endless conveyor chain (not shown) mounted over sprockets (not shown). The sprockets are mounted on shafts 74-78 supported by a frame 79. Sprocket 74 is a drive sprocket which is driven by a motor (not shown). Thus, as will be understood by those skilled in the art, energizing of the drive motor causes the paddles 73 to travel in a clockwise direction, as seen in FIG. 9.

As described above, the diapers 21, after formation, are folded longitudinally and then in half transversely. The formed and folded diapers are delivered, one at a time, from a conveyor 87 to the stacker 71. Although only a few of the diapers 21 are shown on the stacker 71, the conveyor 87 is timed relative to the moving paddles 73 so that one diaper 21 is delivered to each space between adjacent sets of paddles. The formed and folded diapers 21 are delivered by the conveyor 87 with their marginal portions 29 trailing. Thus, the diapers enter the stacker 71 such that the marginal portions 29 are disposed outwardly of the paddles 73. Preferably, the paddles 73 are of a width to support and retain the diapers in their travel and are of a length so that the marginal portions 29 protrude outwardly of the paddles 73, as shown, and the ribbons 41 are disposed substantially transversely of the travel direction thereof, and are in an unrestrained state, i.e., no draw or stress, so that the ribbons 41 are free to shrink.

As shown in FIG. 9, the diapers 21 on the stacker 71 progress in a clockwise direction so that the marginal portions 29 thereof move closely past the infrared radiant heaters 53-61. The infrared rays generated by the bank of heaters 53-61 and the hot air act on the marginal portions 29 of the diapers, and particularly the ribbons 41 which are secured thereto. As a result, the ribbons 41 absorb the energy of the electromagnetic radiation and are excited and become heated. When the ribbons reach their activation temperature, they shrink and become elasticized. The unrestrained and heat softened state of the diaper marginal portions 29 allows the heat shrinkable material to overcome the resistant force in the diaper material to which it is attached thereby giving the maximum amount of elasticity available.

The radiant heaters 53-61 can be of any suitable construction capable of generating infrared rays at the desired wavelength and intensity, and may include or be adapted for communication with a source of heated air. The heaters and air source are constructed and arranged such that the infrared rays and hot air act upon and substantially uniformly heat the entire length of the ribbons 41. Desirably, the heaters 53-61 are adjustable toward and away from the stacker 71 by suitable means as will be understood by those skilled in the art.

As described above, the ribbons 41 can be constructed of a polyether block amide (PEBA), EVA ionomer or EAA skin coated material which contains carbonyl, ether, amide and methylene functional groups. This material is highly absorptive of electromagnetic radiation at a wavelength of from about 1.0 to about 14.0 microns. The outer poly layer of this material melts at about 230° F. so that the heated air should not exceed about 220° F. Under these conditions, the outer poly is softened to minimize inhibition to the shrink process without becoming damaged. In addition, the convection air, which is somewhat cooler than the radiation heater elements, serves a useful cooling purpose.

The total length of feed path of the diapers which is exposed to infrared radiation and hot air is determined by such factors as the speed of travel of the stacker, the capacity and intensity of the radiant heaters, the temperature and flow volume of hot air, the space between the radiant heaters and the marginal diaper portions 29, and the particular material employed in the ribbons 41. Use is made of the fact that the marginal diaper portions 29 and the ribbons 41 are disposed transversely of the travel direction so that a maximum amount of "dwell" time, i.e., time of exposure of the ribbons is achieved with a minimum of radiation heaters. For the coextruded PEBA/EVA ionomer material described above, using quartz tungsten or ceramic heaters developing power and spectral distribution as described above, particularly radiation wavelengths of from about 1.0 to about 14.0 microns and preferably about 5.7 to about 5.9 microns, and spacing the heaters about 3.5" from the marginal diaper portions 29, the "dwell time" of the ribbons is preferably about 3 to 5 seconds.

Highly suitable quartz-type radiant heaters useful in this invention include high density, modular panel-type heating units that include combined radiant/convection heating. These heaters include a forced-air flow system which allows the heater to operate efficiently at very high-power levels, as well as making the shrinking process more efficient. One commercial version of this quartz-type heater is the Model No. 4553A-16-6 high density Pyropanel heater marketed by the Energy Systems Division of Research, Inc., Minneapolis, Minn. and is described in U.S. Pat. No. 3,436,524. This unit uses six 1600 watt lamps operating at 240 volts and is adapted for use with a forced air blower which produces 67 SCFM air flow. The lamps exhibit spectral distribution substantially as shown in FIG. 13.

A further embodiment of the invention employed quartz lamps (emitters) which were custom manufactured or tailored by a suitable vendor, such as GTE Sylvania, to meet desired specifications. For example, a custom manufactured lamp, which has been used in the method and apparatus of the present invention, had the following characteristics: The lamp was rated at 1200 watts but was operated with 450 watts of input power. About 50 watts were dissipated as heat, about 130.5 watts were radiated at wavelengths ranging from about 1.5-3 micrometers (microns), about 142.5 watts were radiated at wavelengths ranging from 3-6 micrometers and about 273 watts were radiated at wavelengths outside the range of 1.5-6 micrometers. The peak wavelength of the emission spectrum was at about 3.85 micrometers.

Another very suitable radiant heater includes ceramic-type heaters such as those entitled Sylva-Therm Infrared Ceramic Heaters marketed by GTE Sylvania, Emissive Products, Exeter, N.H. Particularly useful GTE Sylvania products are Model Nos. FSR/122, Part No. IFR 130107 and FRS/245, Part No. IFR 130103. The individual ceramic heaters identified here are 220 volt units operating at 500 watts and 1000 watts, respectively. On the graph of FIG. 12, the main wavelength of Model No. FSR/122 is determined using the right-hand ordinate. On the graph of FIG. 12, the main wavelength of Model No. FSR/245 is determined using the left-hand ordinate.

In the processing of the diapers according to the method of this invention, the individual diapers 21, after having been formed and folded as described, are delivered by the conveyor 87 to the stacker 71 and are positioned between adjacent paddles 73 so that the marginal portions 29 are disposed outwardly and are in an unrestrained state. The stacker 71 transports the diapers past the bank of infrared heaters 53-61, the latter causing the diaper marginal portions 29 to be acted upon with electromagnetic radiation and hot air if desired. The PEBA material and its skin layers in the thermally-elasticizable ribbons 41 are highly absorptive of the generated electromagnetic radiation which is at a wavelength of from about 1.0 to about 14.0, and preferably from about 5.7 to about 5.9 microns. This causes the ribbons 41 to be heated to their activation temperature, i.e., from about 125° F. to about 230° F., and preferably from about 180° F. to about 200° F. Upon heating, the ribbons 41 shrink, as described above, to provide the elasticity desired in the marginal portions 29 of the diapers 21.

After the ribbons 41 are heat shrunk and when the diapers 21 progress past the last heater 61, the diapers can be removed from the stacker 71 by a suitable stripping means (not shown). Preferably, and as will be understood by those skilled in the art, the finished diapers 21 can be ejected in stacks onto a support surface 81 and packed into suitable containers.

(d) Operational Conditions

It has been determined that the thermally-elasticizable strips should be heated to a temperature in the range of about 125° F. to about 230° F., although temperatures outside this range can be used depending upon the material used for the strips. In the present invention, this temperature is achieved in the ribbons 41 with minimal effect such as thermal damage to the layers of the diapers. Furthermore, heating of the elasticizable ribbons 41 is achieved in the present invention with minimum heating of the surrounding air and stacker structure such as the stacker fingers. Thus, the radiant energy is used most efficiently and is not wasted, and the coefficient of friction between the diapers and the stacker finger is not affected.

Advantageously, the thermally-elasticizable ribbons 41 are heated and activated with substantially no interference or slowdown in the diaper forming, stacking, and packaging process. As described, the stacker 71 is used to arrange the diapers in stacks for subsequent packaging. By providing the bank of infrared heaters adjacent the stacker, together with the utilization of heated air, no additional processing time or space is required in the process.

Still further, it will be appreciated that the diapers 21 are processed one at a time during their formation and folding sequence and travel at a very high linear speed throughout this process. It will be appreciated that the diapers move at a substantially reduced linear speed through the stacker (since they are arranged transversely to the feed direction) and that heating to the activation temperature of the ribbons 41 can be achieved in this zone by heaters which extend over a reduced conveyor length. Thus, a dwell time of 3 to 5 seconds is achieved by a substantially reduced bank of heaters as would be required if activation of the ribbons 41 were achieved during longitudinal and linear travel of the diapers.

By the foregoing, there has been disclosed a method and apparatus for activating heat shrinkable ribbon on disposable garments and other articles calculated to fulfill the inventive objects set forth and inherent herein. While preferred embodiments of the invention are described, it will be apparent to those skilled in the art that various additions, substitutions, modifications and omissions can be made to the present invention without departing form the scope or spirit of the invention. Thus, it is intended that the present invention cover those additions, substitutions, modifications and omissions provided they come within the scope of the appended claims and their equivalents.

What is claimed is:

1. An apparatus for activating a thermally-elasticizable ribbon which is absorptive of infrared radiation and is located on a layer of an article, comprising:

conveyor means for feeding a plurality of articles having thermally-elasticizable ribbons located thereon, said conveyor means including means for holding said articles in spaced relation, with said elasticizable ribbons presented outwardly of said conveyor means in an unrestrained state;

infrared radiation means disposed adjacent said conveyor means for irradiating said elasticizable ribbons with infrared radiation; and means for maintaining a desired spectral distribution of said infrared radiation which excites functional groups within said elasticizable ribbons and thereby primarily heats said ribbons to an activation temperature at which the ribbons shrink while substantially not affecting said article layer, wherein said maintaining means comprises means for directing heated convection air past said infrared radiation means toward said articles to thereby cool said infrared radiation means and maintain said desired spectral distribution while also providing a softening of said article layer.

2. An apparatus as recited in claim 1, wherein said means for maintaining said desired infrared spectral distribution includes means for varying the operating temperature of said infrared radiation means.

3. An apparatus as recited in claims 1, wherein said maintaining means is constructed to soften said article layer without affecting a coefficient of friction between said article and said conveyor means.

4. The apparatus claimed in claim 1, said conveyor means being substantially continuous in operation, said infrared radiation means being stationary and extending along a length of said conveyor means, whereby said ribbons are bombarded by said infrared rays and heated convection air for a predetermined time period causing said ribbon to be heated to said activation temperature.

5. The apparatus claimed in claim 1, including means for adjusting the spacing between the infrared radiation means and said conveyor.

6. The apparatus claimed in claim 1, said ribbons being constructed of a polyether block amide material which contains a carbonyl group, said infrared radiation means generating radiation including wavelengths of from about 1.0 to about 14.0 microns.

7. The apparatus claimed in claim 6, said infrared radiation means generating radiation including wavelengths of from about 5.7 to about 5.9 microns.

8. An apparatus as recited in claim 1, wherein said ribbons are constructed of a coextruded polyether block amide/ethylene vinyl acetate ionomer which contains one or more functional groups selected from the group consisting of carbonyl, ether, amide and methylene.

9. The apparatus claimed in claim 1, said ribbons being constructed of a material selected from the group consisting of polyurethanes based upon polyethers and polyesters, ethylene/vinyl acetate copolymers, modified natural rubber elastomers, polyester block amides, polyether block amides, polyvinyl chlorides, polyester polyether copolymers, ethylene/propylene copolymers and blends, and complex composite materials constructed of EVA polyethylene/polyvinyl acetate copolymers.

10. The apparatus claimed in claim 9, said infrared radiation means comprising a bank of heaters positioned along the direction of travel of said conveyor means.

11. The apparatus claimed in claim 1, said conveyor means comprising a plurality of spaced paddles extending outwardly of said conveyor means and adapted to receive and support said articles between adjacent paddles with the edges of said articles containing said ribbons positioned outwardly of said paddles, said infrared radiation means being disposed adjacent to and spaced from the outer ends of said paddles.

12. The apparatus claimed in claim 1, said conveyor means constructed to support said article with said ribbons disposed substantially transverse to the direction of movement of said conveyor means.

* * * * *